(12) United States Patent
Mueller et al.

(10) Patent No.: US 9,346,958 B2
(45) Date of Patent: *May 24, 2016

(54) REACTIVE DYES, THEIR PREPARATION AND THEIR USE

(71) Applicant: Huntsman International LLC, The Woodlands, TX (US)

(72) Inventors: Alexander Mueller, Weil am Rhein (DE); Kurt Plattner, Gelterkinden (CH); Damien Schoehn, Ensisheim (FR); Rainer Hildebrand, Lorrach (DE)

(73) Assignee: Huntsman International LLC, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,563

(22) PCT Filed: Apr. 25, 2013

(86) PCT No.: PCT/EP2013/058565
§ 371 (c)(1),
(2) Date: Nov. 12, 2014

(87) PCT Pub. No.: WO2013/182349
PCT Pub. Date: Dec. 12, 2013

(65) Prior Publication Data
US 2015/0143639 A1    May 28, 2015

(30) Foreign Application Priority Data
Jun. 5, 2012   (EP) ..................................... 12170832

(51) Int. Cl.
| | |
|---|---|
| D06P 5/17 | (2006.01) |
| C09B 62/095 | (2006.01) |
| C09B 62/44 | (2006.01) |
| D06P 1/38 | (2006.01) |
| D06P 3/24 | (2006.01) |
| D06P 3/66 | (2006.01) |
| C07F 11/00 | (2006.01) |
| D06P 1/384 | (2006.01) |
| D06P 5/30 | (2006.01) |

(52) U.S. Cl.
CPC ............. *C09B 62/095* (2013.01); *C07F 11/005* (2013.01); *C09B 62/4416* (2013.01); *D06P 1/38* (2013.01); *D06P 1/384* (2013.01); *D06P 3/248* (2013.01); *D06P 3/66* (2013.01); *D06P 5/30* (2013.01)

(58) Field of Classification Search
CPC ..... C09B 62/095; C07F 11/005; C06P 1/384; C06P 5/30; C06P 3/248
USPC ............................................................ 8/466
See application file for complete search history.

(56) References Cited

U.S. PATENT DOCUMENTS

| | | | |
|---|---|---|---|
| 8,348,412 B2 * | 1/2013 | Hildebrand et al. ......... | 347/100 |
| 2007/0033746 A1 | 2/2007 | Somogyi et al. | |

FOREIGN PATENT DOCUMENTS

| | | | | |
|---|---|---|---|---|
| GB | 1 576 237 | 10/1980 | | |
| WO | 2006/042802 | 4/2006 | | |
| WO | WO 2006/042802 A1 * | 4/2006 | ............. | C09B 62/44 |

OTHER PUBLICATIONS

STIC Search Report dated Mar. 9, 2015.*

* cited by examiner

*Primary Examiner* — Eisa Elhilo

(57) ABSTRACT

Reactive dyes of, for example, formula (101) especially suitable for dyeing synthetic polyamide fibre materials and which yield dyeings or prints having good wet-fastness properties, and a process for their preparation.

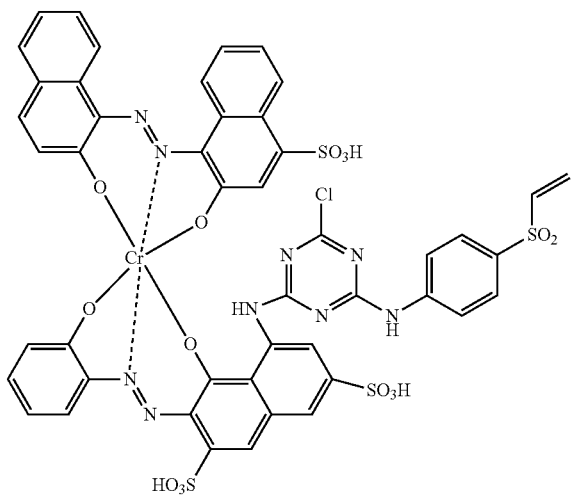

(101)

5 Claims, No Drawings

REACTIVE DYES, THEIR PREPARATION AND THEIR USE

CROSS REFERENCE TO RELATED APPLICATIONS

This application is the National Phase of International Application PCT/EP2013/058565 filed Apr. 25, 2013 which designated the U.S. and which claims priority to European Pat. App. No. 12170832.5 filed Jun. 5, 2012. The noted applications are incorporated herein by reference.

The present invention relates to novel navy blue reactive dyes, to a process for their preparation and to their use in the dyeing or printing of textile fibre materials.

The practice of dyeing using reactive dyes has recently led to higher demands being made on the quality of the dyeings and the economic efficiency of the dyeing process. As a result, there continues to be a need for novel reactive dyes having improved properties, especially in respect of their application.

Dyeing nowadays requires reactive dyes that have sufficient substantivity and at the same time have good ease of washing off of unfixed dye. They should also have a good colour yield and high reactivity, the objective being to provide especially dyeings having high degrees of fixing. The known dyes do not satisfy those requirements in all properties.

Deep coloured dyeings on polyamide could be achieved hitherto only using acid dyes, but such dyeings are not fast to wetting at elevated temperatures. Deep dyeings that are simultaneously permanently fast to wetting can be obtained only by using reactive dyes.

The problem underlying the present invention is accordingly to find, for the dyeing and printing of fibre materials, novel improved reactive dyes having the qualities characterised above to a high degree, especially when the dyes are used for dyeing synthetic polyamide fibre materials. The novel dyes should be distinguished by high fixing yields and high fibre-dye binding stabilities. The dyes should especially yield dyeings having good allround fastness properties, for example fastness to light, fastness to wetting and fastness to chlorine.

In particular, there is a need for highly brilliant reactive dyes which are suitable for dyeing microfibres of synthetic polyamides and provide dyeings having high fastness to light and to wetting, especially in navy blue shades.

It has been found that the problem posed is largely solved by the novel dyes defined hereinbelow.

The present invention accordingly relates to a reactive dye of formula

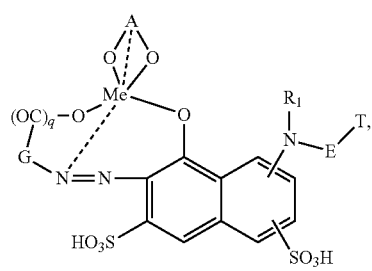

(1)

wherein Me is chromium, cobalt or iron,
$R_1$ is hydrogen or unsubstituted or substituted $C_1$-$C_4$alkyl, E is a bivalent radical of formula

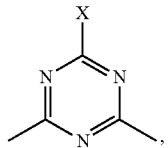

(1a)

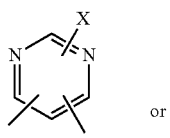

(1b)

or

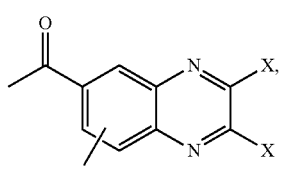

(1c)

wherein X denotes chlorine or fluorine,

T is a fibre-reactive radical of formula

—NH—$(CH_2)_{2-3}$—$SO_2$—Z, (2a)

—NH—$(CH_2)_{2-3}$—O—$(CH_2)_{2-3}$—$SO_2$—Z, (2b)

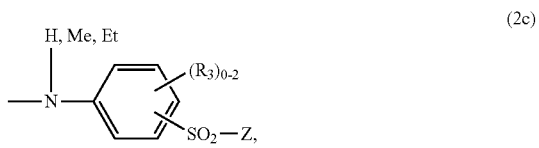

(2c)

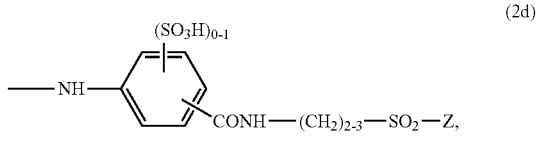

(2d)

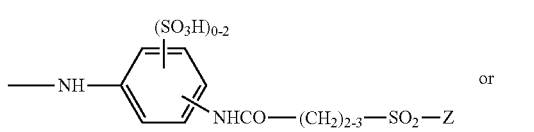

or (2e)

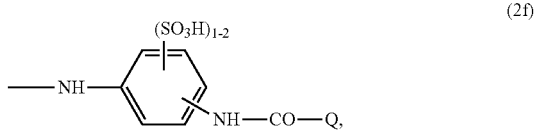

(2f)

$(R_3)_{0-2}$ denotes from 0 to 2 identical or different substituents from the group halogen, $C_1$-$C_4$alkyl, $C_1$-$C_4$alkoxy and sulfo, Z is vinyl or a —$CH_2$—$CH_2$—U radical and U is a group that is removable under alkaline conditions, Q is a —CH(Hal)-$CH_2$-Hal or —C(Hal)=$CH_2$ group, q is the number 0 or 1, G is a bivalent radical of formula

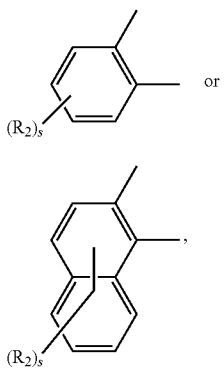

wherein $(R_2)_s$ denotes s identical or different substituents from the group halogen, nitro, unsubstituted or halo-substituted $C_1$-$C_4$alkyl, $C_2$-$C_4$alkanoylamino, $C_1$-$C_4$alkylsulfonyl, carbamoyl, sulfamoyl, sulfo and -E-T, wherein E and T are as defined above,
s is the number 0, 1, 2 or 3,
A denotes a bivalent radical of formula

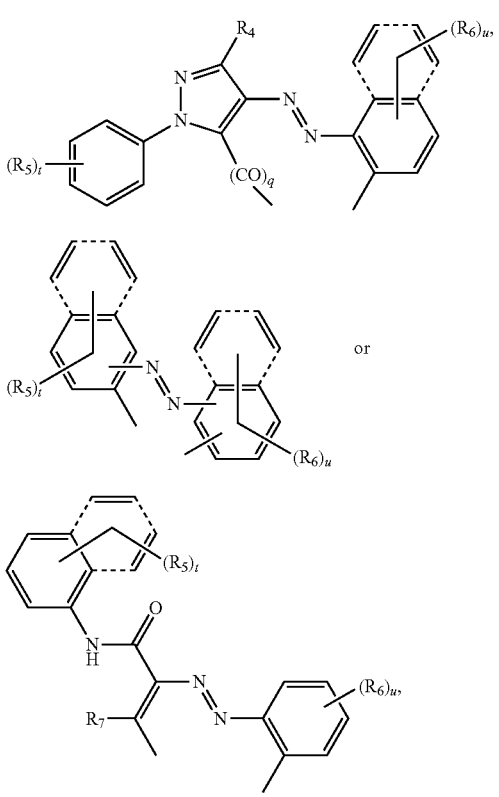

wherein $R_1$, $R_2$, X, T, m, n, q and s are as defined above,
$R_4$ and $R_7$ denote hydrogen, $C_1$-$C_4$alkyl, —COOH or —COO—$C_1$-$C_4$alkyl,
$R_5$ and $R_6$ represent, each independently of the other, identical or different substituents from the group hydroxyl, halogen, nitro, unsubstituted or halo-substituted $C_1$-$C_4$alkyl, $C_1$-$C_4$alkoxy, $C_2$-$C_4$alkanoylamino, $C_1$-$C_4$alkylsulfonyl, carbamoyl, sulfamoyl and sulfo, and t and u are each independently of the other the number 0, 1, 2 or 3.

In the radical of formula (2c), Me is the methyl radical and Et the ethyl radical. The said radicals are, in addition to hydrogen, suitable as substituents on the nitrogen atom.

As $C_1$-$C_4$alkyl there comes into consideration for $R_1$ to $R_7$, each independently of any other(s), for example, methyl, ethyl, n-propyl, isopropyl, n-butyl, sec-butyl, tert-butyl or isobutyl, preferably methyl or ethyl and especially methyl. In the case of $R_1$, the mentioned alkyl radicals are unsubstituted or substituted, for example, by hydroxy, sulfo, sulfato, cyano, carboxy, $C_1$-$C_4$alkoxy or by phenyl, preferably by hydroxy, sulfato, $C_1$-$C_4$alkoxy or by phenyl. For $R_1$, the corresponding unsubstituted radicals are preferred.

As $C_1$-$C_4$alkyl there comes into consideration for $R_2$, $R_5$ and $R_6$, for example, methyl, ethyl, n-propyl, isopropyl, n-butyl, sec-butyl, tert-butyl or isobutyl, preferably methyl or ethyl and especially methyl. The mentioned alkyl radicals are unsubstituted or mono- or poly-substituted by halogen, for example by fluorine, chlorine or bromine, preferably by fluorine or chlorine.

As $C_1$-$C_4$alkoxy there comes into consideration for $R_3$, for example, methoxy, ethoxy, n-propoxy, isopropoxy, n-butoxy or isobutoxy, preferably methoxy or ethoxy and especially methoxy.

As halogen there comes into consideration for $R_2$, $R_3$, $R_5$ and $R_6$, each independently of any other(s), for example, fluorine, chlorine or bromine, preferably chlorine.

As $C_2$-$C_4$alkanoylamino there comes into consideration for $R_2$, for example, acetylamino or propionylamino, preferably acetylamino.

As $C_1$-$C_4$alkylsulfonyl there comes into consideration for $R_2$, $R_5$, and $R_6$, for example, methylsulfonyl, ethylsulfonyl, n-propylsulfonyl, isopropylsulfonyl or n-butylsulfonyl, preferably methylsulfonyl or ethylsulfonyl.

$R_2$, $R_5$ and $R_6$ denoting carbamoyl corresponds to a radical of formula —$CONH_2$.

$R_2$, $R_5$ and $R_6$ denoting sulfamoyl corresponds to a radical of formula —$SO_2NH_2$.

$R_1$ is preferably hydrogen.

Preferably, $(R_2)_s$ denotes s identical or different substituents from the group halogen, nitro, $C_2$-$C_4$alkanoylamino and sulfo, especially nitro and sulfo and more especially nitro.

Preferably, $(R_3)_{0-2}$ denotes from 0 to 2 identical or different substituents from the group $C_1$-$C_4$alkyl, $C_1$-$C_4$alkoxy and sulfo, especially methyl, methoxy and sulfo.

Especially preferably formula (2c) contains no substituent $R_3$.

T is preferably a radical of formula (2c), (2d), (2e) or (2f), especially of formula (2c) or (2d) and more especially of formula (2c).

Hal in the fibre-reactive radical of formula (2f) is preferably chlorine or bromine, especially bromine.

As leaving group U there comes into consideration, for example, —Cl, —Br, —F, —$OSO_3H$, —$SSO_3H$, —OCO—$CH_3$, —$OPO_3H_2$, —OCO—$C_6H_5$, —$OSO_2$—$C_1$-$C_4$alkyl or —$OSO_2$—$N(C_1$-$C_4$alkyl$)_2$. Preferably, U is a group of formula —Cl, —$OSO_3H$, —$SSO_3H$, —OCO—$CH_3$, —OCO—$C_6H_5$ or —$OPO_3H_2$, especially —Cl or —$OSO_3H$.

Examples of suitable radicals Z are accordingly vinyl, β-bromo- or β-chloro-ethyl, β-acetoxyethyl, β-benzoyloxyethyl, β-phosphatoethyl, β-sulfatoethyl and β-thiosulfatoethyl. Z is preferably vinyl, β-chloroethyl or β-sulfatoethyl and especially vinyl.

s is preferably the number 0, 1 or 2, especially the number 0 or 1 and more especially the number 0.

q is preferably the number 0.

Me is preferably chromium.

E is preferably a bivalent radical of formula

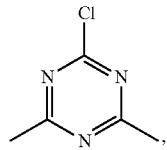
(1a1)

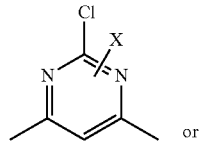
(1b1) or

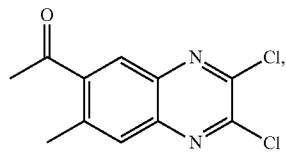
(1c1)

in particular a radical of formula (1a1).

The radical of formula (2c) is preferably a radical of formula

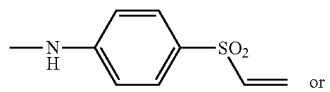
(2c1) or

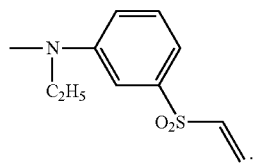
(2c2)

A preferably denotes a bivalent radical of formula

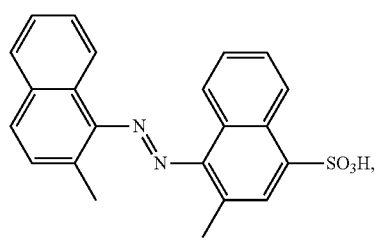
(3b1)

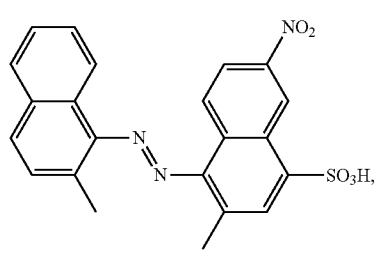
(3b2)

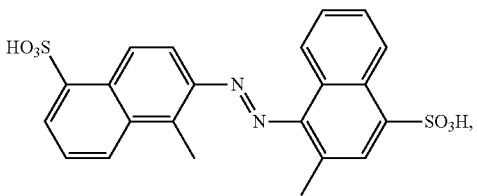
(3b3)

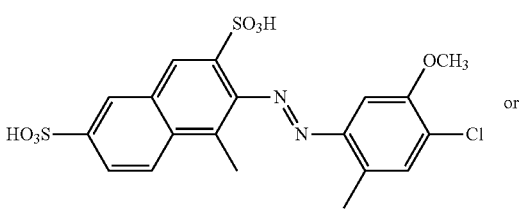
(3b4) or

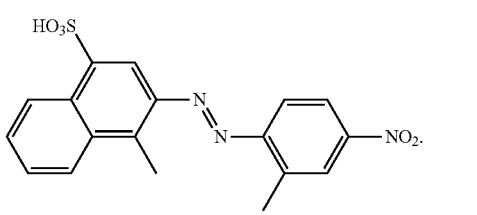
(3b5)

In formula (1) the substituent $-NR_1$-ET is preferably in the 8-position of the naphthaline group wherein the oxygen atom is bound to the 1-position.

In formula (1) the second sulfo substituent is preferably in the 5-position or the 6-position of the naphthaline group, most preferably in the 6-position, wherein the oxygen atom is bound to the 1-position.

The invention further relates to a process for the preparation of a reactive dye of formula (1) as defined above, wherein E is a radical of formula (1a), which comprises
(i) preparing from the compounds of formulae HO-A-OH    (4) and

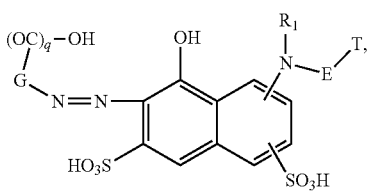
(5)

using a suitable chromium, cobalt or iron compound, the 1:2 metal complex dye of formula

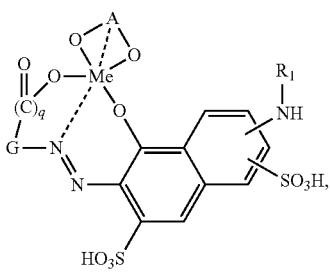
(6)

and (ii) in a first condensation step, condensing the 1:2 metal complex dye of formula (6) obtained according to (i) with a cyanuric halide of formula

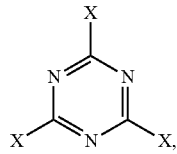
(7)

and (iii) in a second condensation step, condensing the primary condensation product of formula

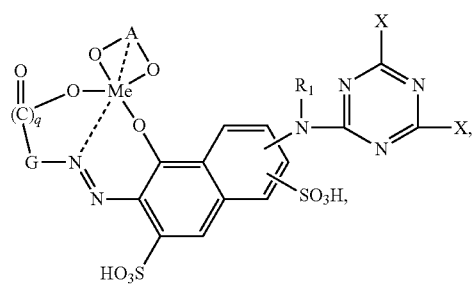
(8)

obtained according to (ii) with a compound of formula

T-H (9), or (iv) condensing the 1:2 metal complex dye of formula (6) obtained according to (i) with a compound of formula

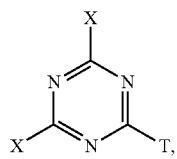
(10)

$R_1$, Me, X, T, A, G and q each having the definitions given above.

A suitable cyanuric halide of formula (6) is cyanuric chloride.

The compound of formula (10) is known or can be prepared in analogy to known processes, for example by condensation of a cyanuric halide of formula (6) with a compound of formula (9) wherein T has the definitions and preferred meanings given above.

1:2 chromium complex dyes of formula (6) are known or can be obtained in analogy to known compounds, for example by reacting a 1:1 chromium complex compound of formula

(11)

with an azo compound of formula (5), A, G, T, $R_1$ and q each having the definitions and preferred meanings given hereinbefore.

The reaction of the 1:1 chromium complex compound of formula (11) with an azo compound of formula (5) is carried out, for example, in aqueous medium at a temperature of, for example, from 40 to 130° C., especially from 70 to 100° C., at a pH value of, for example, from 8 to 14, especially at a pH value of from 10 to 13. The reaction is more advantageously carried out in the presence of a mineral-acid-neutralising or alkaline medium, for example in the presence of an alkali metal carbonate, alkali metal acetate or alkali metal hydroxide, the preferred alkali metal being sodium.

If A is not a symmetrical radical, the 1:2 metal complex of formula (6) prepared in accordance with (i) usually includes two coordination isomers.

In addition to the metal complexes disclosed in the form of formulae in the context of the present invention, for example of formulae (1), (6) and (8), the disclosure is to be regarded as also including the corresponding coordination isomers.

The compounds of formulae (4), (5), (9) and (11) are known or can be obtained in analogy to known processes.

For example, 1:1 chromium complex compounds of formula (11) can be obtained according to conventional chromination processes, in which the reaction with a chromium salt can be performed, for example, in aqueous medium, optionally under pressure, at a temperature of, for example, from 90 to 130° C. Suitable chromium salts are, for example, chromium(III) acetate, chromium(III) nitrate, chromium(III) chloride, chromium(III) salicylate and chromium(III) sulfate.

Compounds of formulae (4) and (5) can be obtained according to customary diazotisation and coupling reactions. The diazotisation is generally carried out by action of nitrous acid in aqueous mineral acid solution at low temperature, for example from 0 to 20° C., and the coupling advantageously at alkaline pH values, for example at pH values of from 8 to 12.

The 1:2 cobalt or iron complex dyes of the azo compounds of formulae (4) and (5) are known or can be obtained in analogy to known processes.

The 1:2 chromium or 1:2 cobalt complex dyes can be obtained, for example, analogously to the processes mentioned in GB-A-716 753, GB-A-719 274, GB-A-745 641 and GB-A-851 861. The 1:2 iron complex dyes can be obtained, for example, analogously to the process mentioned in U.S. Pat. No. 5,376,151.

The condensation reactions are carried out in a manner known per se, usually in aqueous solution at a temperature of, for example, from 0 to 50° C. and a pH value of, for example, from 2 to 10.

The condensation of the 1:2 metal complex dye of formula (6) with the cyanuric halide of formula (7) according to (ii) is preferably carried out at a temperature of from 0 to 5° C. and a pH value of from 3 to 6. The condensation of the primary condensation product of formula (8) with the compound of formula (9) according to (iii) is preferably carried out at a temperature of from 0 to 30° C. and a pH value of from 4 to 7. The condensation of the 1:2 metal complex dye of formula (5) with a compound of formula (10) according to (iv) is preferably carried out at a temperature of from 20 to 50° C. and a pH value of from 4 to 6.

Formula (1) is understood to include all the various coordination isomers which are generated during the multistage synthesis.

Moreover, formula (1) is understood to include tautomers which may be generated by migration of a proton.

The end product can optionally in addition be subjected to a conversion reaction. Such a conversion reaction is, for example, the conversion of a vinylatable reactive group T (Z or Q) into its vinyl form by treatment with dilute sodium hydroxide solution, such as, for example, the conversion of the β-sulfatoethylsulfonyl or β-chloroethylsulfonyl group into the vinylsulfonyl radical or the conversion of the α,β- dihalopropionylamino group into the α-haloacryloylamino radical. Such reactions are known per se. The conversion reaction is generally carried out in neutral to alkaline medium at a temperature of, for example, from 20 to 70° C., at a pH value of, for example, from 6 to 14.

The reactive dyes of formula (1) wherein E is a radical of formula (1b) or (1c) can be prepared in an analogous manner.

The reactive dyes of formula (1) contain sulfo groups, which are each either in the form of the free sulfo acid or, preferably, in the form of a salt thereof, for example a sodium, lithium, potassium or ammonium salt, or a salt of an organic amine, for example a triethanol-ammonium salt.

The reactive dyes of formula (1) may comprise further additives, for example sodium chloride or dextrin.

The reactive dyes of formula (1) according to the invention may optionally comprise further adjuvants which, for example, improve handling or increase storage stability, such as, for example, buffers, dispersants or anti-dusts. Such adjuvants are known to the person skilled in the art.

The reactive dyes according to the invention are suitable, for example, for dyeing or printing hydroxyl-group-containing or nitrogen-containing fibre materials. Examples that may be mentioned are silk, wool, cellulosic fibre materials of all kinds and polyurethanes, as well as polyamide fibres. Cellulosic fibre materials are, for example, natural cellulosic fibres, such as cotton, linen and hemp, and also cellulose and regenerated cellulose. The reactive dyes according to the invention are also suitable for dyeing or printing hydroxyl-group-containing fibres present in blend fabrics, e.g. blends of cotton with polyester fibres or polyamide fibres.

Preference is given to the dyeing or printing of natural or synthetic polyamide fibre materials, especially synthetic polyamide fibre materials, such as, for example, polyamide 6 (poly-ε-caprolactam), polyamide 6,6 (polyhexamethylene-adipic acid amide), polyamide 7, polyamide 6,12 (polyhexamethylenedodecanoic acid amide), polyamide 11 or polyamide 12, copolyamides with polyamide 6,6 or polyamide 6, such as, for example, polymers of hexamethylenediamine, ε-caprolactam and adipic acid and polymers of adipic acid, hexamethylenediamine and isophthalic acid or of adipic acid, hexamethylenediamine and 2-methylpentamethylenediamine or 2-ethyltetramethylenediamine. The reactive dyes of formula (1) according to the invention are furthermore suitable for dyeing or printing blend fabrics or yarns of synthetic polyamide and wool.

The process according to the invention is advantageously suitable also for dyeing or printing microfibres of synthetic polyamides. Microfibres are understood to mean fibre materials that are made up of threads having an individual fineness of less than 1 denier (1.1 dTex). Such microfibres are known and are usually prepared by melt-spinning.

The said textile material can be in a very wide variety of processing forms, for example in the form of fibres, yarn, woven fabrics or knitted fabrics and in the form of carpets.

The reactive dyes of formula (1) can be used for dyeing or printing according to customary dyeing and printing methods. In addition to comprising water and the dyes, the dyeing liquors or print pastes may comprise further additives, for example wetting agents, anti-foams, levelling agents or agents that influence the property of the textile material, for example softeners, additives for flame-resistant finishes or dirt-, water- and oil-repellents and also water softeners and natural or synthetic thickeners, for example alginates and cellulose ethers.

In the case of woven carpet material, printing methods such as displacement printing or space dyeing are important.

Preference is given to dyeing, which is carried out especially according to the exhaust method and, in the case of carpet-dyeing, can also be carried out according to the continuous method.

Dyeing is preferably carried out at a pH value of from 2 to 7, especially from 2.5 to 5.5 and more especially from 3 to 4.5. The liquor ratio can be chosen within a wide range, for example from 1:5 to 1:50, preferably from 1:5 to 1:30. Dyeing is preferably carried out at a temperature of from 80 to 130° C., especially from 85 to 120° C.

The reactive dyes of formula (1) yield level dyeings having good allround properties, for example good fastness to chlorine, to rubbing, to wetting, to wet-rubbing, to washing, to water, to sea water and to perspiration, and good fastness to light. They are also distinguished by uniform colour build-up, good affinity, high reactivity, good fixing ability and a very good build-up ability. The dyes according to the invention have good water-solubility and are readily combinable with other dyes.

The dyes of formula (1) according to the invention are also suitable as colorants for use in recording systems. Such recording systems are, for example, commercially available ink-jet printers for paper or textile printing, or writing instruments, such as fountain pens or ballpoint pens, and especially ink-jet printers. For that purpose, the dyes according to the invention are first brought into a form suitable for use in recording systems. A suitable form is, for example, an aqueous ink, which comprises the dyes according to the invention as colorants. The inks can be prepared in customary manner by mixing together the individual components in the desired amount of water.

As substrates there come into consideration the above-mentioned hydroxyl-group-containing or nitrogen-containing fibre materials, especially natural or synthetic polyamide fibre materials. The fibre materials are preferably textile fibre materials.

Substrates that also come into consideration are paper and plastics films.

As examples of paper there may be mentioned commercially available ink-jet paper, photo paper, glossy paper, plastics-coated paper, e.g. Epson Ink-jet Paper, Epson Photo Paper, Epson Glossy Paper, Epson Glossy Film, HP Special Ink-jet Paper, Encad Photo Gloss Paper and Ilford Photo Paper. Plastics films are, for example, transparent or cloudy/opaque. Suitable plastics films are, for example, 3M Transparency Film.

Depending on the nature of the use, for example textile printing or paper printing, it may be necessary, for example, for the viscosity or other physical properties of the ink, especially properties that have an influence on the affinity for the substrate in question, to be adapted accordingly.

The dyes used in the aqueous inks should preferably have a low salt content, that is to say they should have a total content of salts of less than 0.5% by weight, based on the weight of the dyes. Dyes that have relatively high salt contents as a result of their preparation and/or as a result of the subsequent addition of diluents can be desalted, for example by membrane separation procedures, such as ultrafiltration, reverse osmosis or dialysis.

The inks preferably have a total content of dyes of from 1 to 35% by weight, especially from 1 to 30% by weight and preferably from 1 to 20% by weight, based on the total weight of the ink. The preferred lower limit in this case is 1.5% by weight, preferably 2% by weight and especially 3% by weight.

The inks may comprise water-miscible organic solvents, for example $C_1$-$C_4$ alcohols, e.g. methanol, ethanol, n-propanol, isopropanol, n-butanol, sec-butanol, tert-butanol or iso-butanol; amides, e.g. dimethylformamide or dimethylacetamide; ketones or ketone alcohols, e.g. acetone or diacetone alcohol; ethers, e.g. tetrahydrofuran or dioxane; nitrogen-containing heterocyclic compounds, e.g. N-methyl-2-pyrrolidone or 1,3-dimethyl-2-imidazolidone, polyalkylene glycols, e.g. polyethylene glycol or polypropylene glycol; $C_2$-$C_6$-alkylene glycols and thioglycols, e.g. ethylene glycol, propylene glycol, butylene glycol, triethylene glycol, thiodiglycol, hexylene glycol and diethylene glycol; other polyols, e.g. glycerol or 1,2,6-hexanetriol; and $C_1$-$C_4$alkyl ethers of polyhydric alcohols, e.g. 2-methoxy-ethanol, 2-(2-methoxyethoxy)ethanol, 2-(2-ethoxyethoxy)ethanol, 2-[2-(2-methoxyethoxy)-ethoxy]ethanol or 2-[2-(2-ethoxyethoxy)ethoxy]ethanol; preferably N-methyl-2-pyrrolidone, diethylene glycol, glycerol or especially 1,2-propylene glycol, usually in an amount of from 2 to 30% by weight, especially from 5 to 30% by weight and preferably from 10 to 25% by weight, based on the total weight of the ink.

In addition, the inks may also comprise solubilisers, e.g. ε-caprolactam.

The inks may comprise thickeners of natural or synthetic origin, inter alia for the purpose of adjusting the viscosity.

Examples of thickeners that may be mentioned include commercially available alginate thickeners, starch ethers or locust bean flour ethers, especially sodium alginate on its own or in admixture with modified cellulose, e.g. methyl cellulose, ethyl cellulose, carboxymethyl cellulose, hydroxyethyl cellulose, methyl hydroxyethyl cellulose, hydroxypropyl cellulose or hydroxypropyl methyl cellulose, especially with preferably from 20 to 25% by weight carboxymethyl cellulose. Synthetic thickeners that may also be mentioned are, for example, those based on poly(meth)acrylic acids or poly(meth)acrylamides and also polyalkylene glycols having a molecular weight of, for example, from 2000 to 20 000, such as, for example, polyethylene glycol or polypropylene glycol or mixed polyalkylene glycols of ethylene oxide and propylene oxide.

The inks comprise such thickeners, for example, in an amount of from 0.01 to 2% by weight, especially from 0.01 to 1% by weight and preferably from 0.01 to 0.5% by weight, based on the total weight of the ink.

The inks may also comprise buffer substances, e.g. borax, borates, phosphates, poly-phosphates or citrates. Examples that may be mentioned include borax, sodium borate, sodium tetraborate, sodium dihydrogen phosphate, disodium hydrogen phosphate, sodium tripolyphosphate, sodium pentapolyphosphate and sodium citrate. They are used especially in amounts of from 0.1 to 3% by weight, preferably from 0.1 to 1% by weight, based on the total weight of the ink, in order to establish a pH value of, for example, from 4 to 9, especially from 5 to 8.5.

As further additives, the inks may comprise surfactants or humectants.

Suitable surfactants include commercially available anionic or non-ionic surfactants. As humectants in the inks according to the invention there come into consideration, for example, urea or a mixture of sodium lactate (advantageously in the form of a 50% to 60% aqueous solution) and glycerol and/or propylene glycol in amounts of preferably from 0.1 to 30% by weight, especially from 2 to 30% by weight.

Preference is given to inks having a viscosity of from 1 to 40 mPa·s, especially from 1 to 20 mPa·s and more especially from 1 to 10 mPa·s.

Furthermore, the inks may in addition comprise customary additives, e.g. anti-foams or especially preservatives that inhibit fungal and/or bacterial growth. Such additives are usually used in amounts of from 0.01 to 1% by weight, based on the total weight of the ink.

As preservatives there come into consideration formaldehyde-yielding agents, for example paraformaldehyde and trioxane, especially aqueous, approximately from 30 to 40% by weight formaldehyde solutions, imidazole compounds, for example 2-(4-thiazolyl)-benzimidazole, thiazole compounds, for example 1,2-benzisothiazolin-3-one or 2-n-octyl-isothiazolin-3-one, iodine compounds, nitriles, phenols, haloalkylthio compounds or pyridine derivatives, especially 1,2-benzisothiazolin-3-one or 2-n-octyl-isothiazolin-3-one. A suitable preservative is, for example, a 20% by weight solution of 1,2-benzisothiazolin-3-one in dipropylene glycol (Proxel® GXL).

The inks may also comprise further additives, such as fluorinated polymers or telomers, for example polyethoxyperfluoroalcohols (Forafac® or Zonyl® products) in an amount of, for example, from 0.01 to 1% by weight, based on the total weight of the ink.

In the case of the ink-jet printing method, individual droplets of ink are sprayed onto a substrate from a nozzle in a controlled manner. It is mainly the continuous ink-jet method and the drop-on-demand method that are used for that purpose. In the case of the continuous ink-jet method, the droplets are produced continuously, droplets not required for the printing operation being discharged into a receptacle and recycled. In the case of the drop-on-demand method, on the other hand, droplets are generated as desired and used for printing; that is to say, droplets are generated only when required for the printing operation. The production of the droplets can be effected, for example, by means of a piezo ink-jet head or by thermal energy (bubble jet). Preference is given to printing by means of a piezo ink-jet head and to printing according to the continuous ink-jet method.

The present invention accordingly relates also to aqueous inks that comprise the dyes of formula (1) according to the invention and to the use of such inks in an ink-jet printing method for printing a variety of substrates, especially textile fibre materials, the definitions and preferences indicated above applying to the dyes, the inks and the substrates.

The following Examples serve to illustrate the invention. Unless otherwise indicated, the temperatures are given in degrees Celsius, parts are parts by weight and percentages relate to % by weight. Parts by weight relate to parts by volume in a ratio of kilograms to liters.

EXAMPLE 1

(a) 26.4 parts of a compound which, in the form of the free acid, corresponds to formula

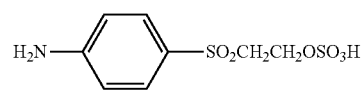

are stirred into 100 parts water. The slurry is cooled to 0° C. by addition of about 50 parts ice and adjusted to pH 3 using aqueous sodium hydroxide solution, the temperature being maintained at 0° C. by cooling with ice. The solution obtained is slowly fed into a slurry of 18.2 parts cyanuric chloride in 20 parts water, about 80 parts ice and 0.2 part $Na_2HPO_4 12H_2O$, the pH being maintained at 3 by addition of an aqueous sodium hydroxide solution and the temperature being maintained at 0° C. by addition of ice. A suspension is obtained whih comprises the compound of formula

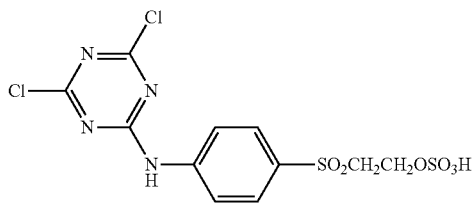

indicated here in the form of the free acid.

(b) 39 parts of a compound which, in the form of the free acid, corresponds to formula

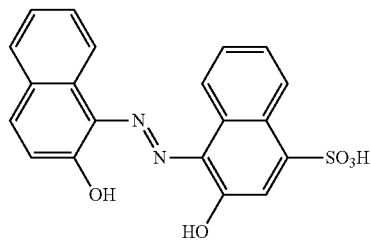 [SMILES: O=S(=O)(O)c1cc(O)c(/N=N/c2c(O)ccc3ccccc23)c2ccccc12]

are made into a slurry with 550 parts water, 15 parts formic acid and 6.8 parts chromium(III) acetate and heated at a temperature of from 100 to 105° C. for 20 hours in an autoclave. The pressure is about 3 bar. After cooling to room temperature, the precipitated product is filtered off, washed with water and dried in vacuo at a temperature of 50° C. A 1:1 complex compound is obtained which, in the form of the free acid, corresponds to formula

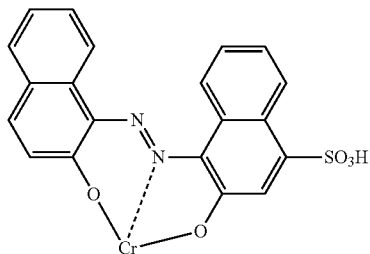

(c) 42.2 parts of the monoazo dye which, in the form of the free acid, corresponds to formula

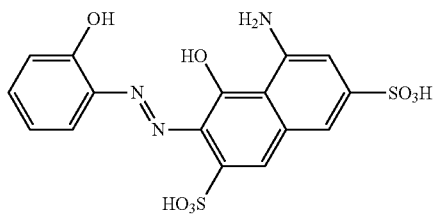 [SMILES: Nc1cc(S(=O)(=O)O)cc2cc(S(=O)(=O)O)c(/N=N/c3ccccc3O)c(O)c12]

and which has been prepared according to customary procedures from diazotised 2-aminophenol and 1-amino-8-naphthol-3,6-disulfonic acid, are stirred together with 47 parts of the chromium complex obtained according to (b) in 600 parts water until homogeneous and heated to 70° C. A pH value of from 8.0 to 8.5 is established and maintained by addition of 2N sodium hydroxide solution. Stirring is then carried out at the above temperature until neither of the two starting compounds can be detected in the resulting clear solution. The isomeric coordination compounds which, in the form of the free acids, correspond to formulae

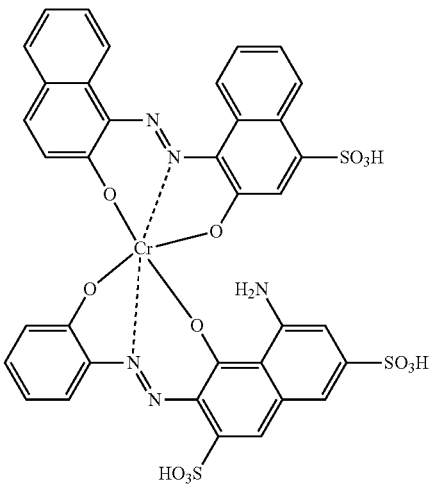

and

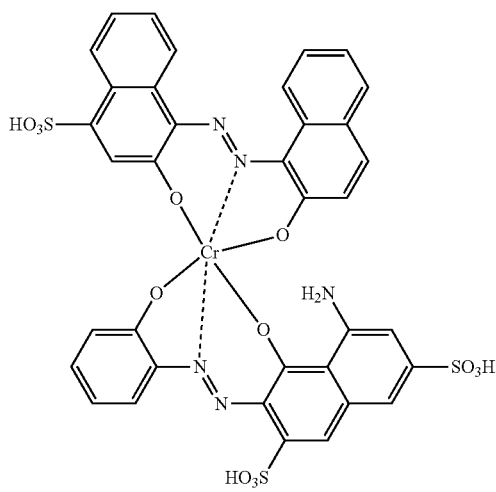

are obtained.

(d) The clear solution is allowed to cool to 50° C., the pH is adjusted to a value of about 5 by addition of aqueous hydrochloric acid, and the suspension obtained according to (a) is slowly added, the pH being maintained at a value of 5 by addition of aqueous sodium hydroxide solution. In order to complete the reaction, stirring is carried out for a further two hours. Subsequently, the solution is treated at room temperature for about two hours with sodium hydroxide at a pH value of 10-11. The solution obtained is freed of salt by dialysis at pH 6 to 7 and concentrated to dryness by evaporation. A dye is obtained which, in the form of the free acid, corresponds to the compound of formula (101)
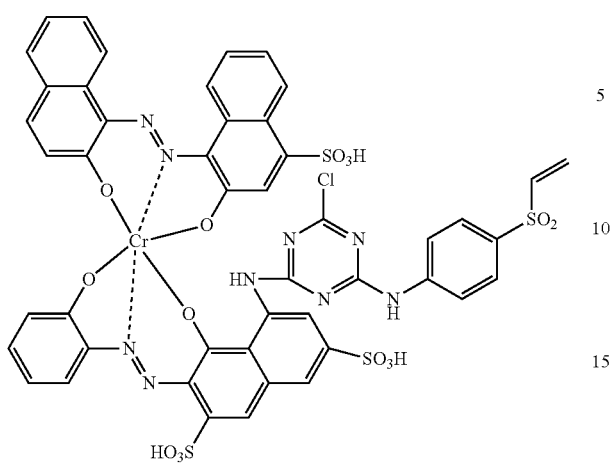
and the coordination isomer thereof ($\lambda_{max}$=586 nm) and yields dyeings or prints on amino-group-containing fibres in navy shades having very good allround fastness properties.
EXAMPLES 2 TO 12
The dyes of formulae
(102)
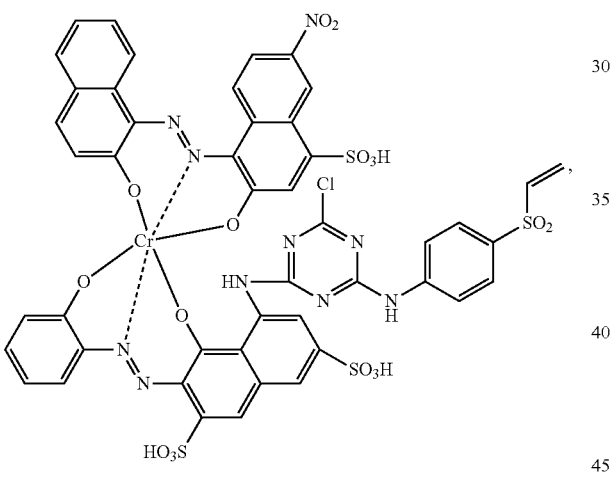
($\lambda_{max}$ = 577 nm)
(103)
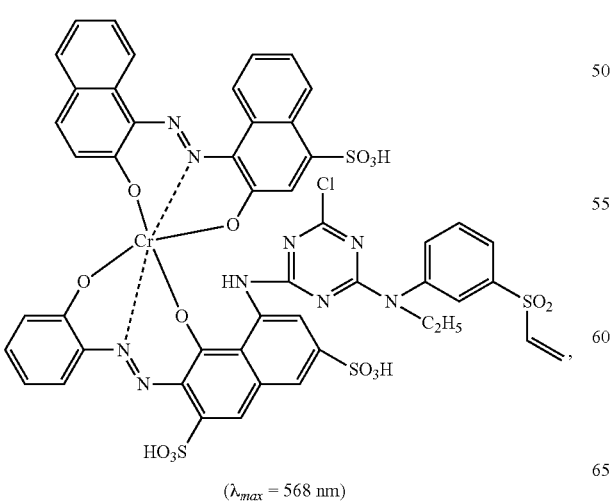
($\lambda_{max}$ = 568 nm)
(104)
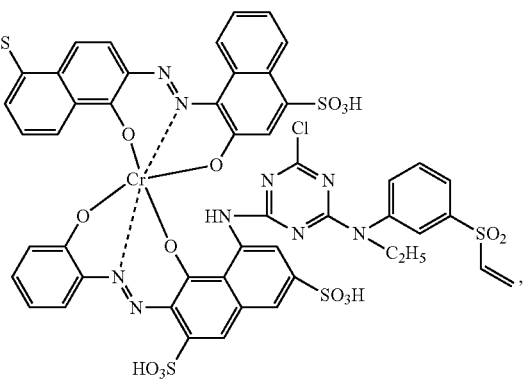
($\lambda_{max}$ = 580 nm)
(105)
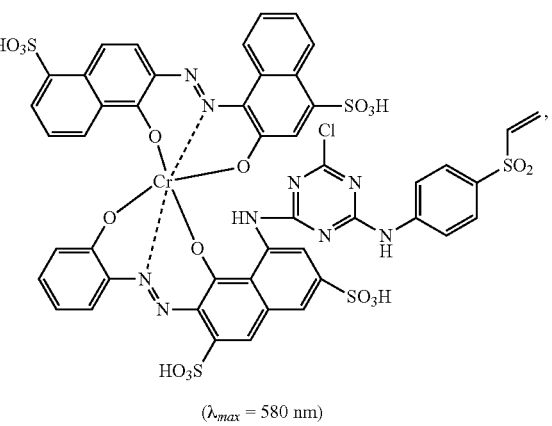
($\lambda_{max}$ = 580 nm)
(106)
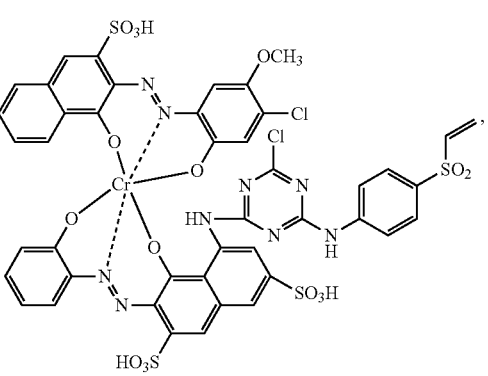
($\lambda_{max}$ = 574 nm)

(107)

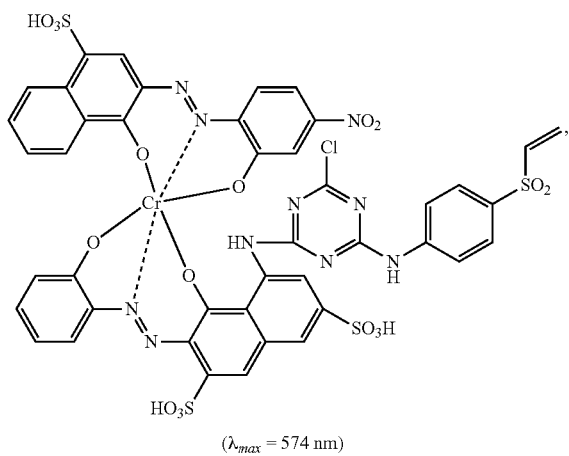

($\lambda_{max}$ = 574 nm)

(108)

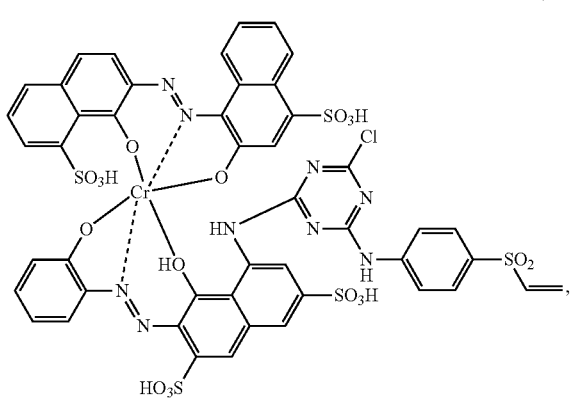

(109)

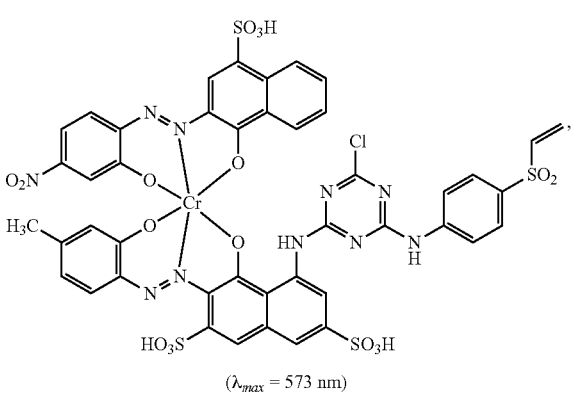

($\lambda_{max}$ = 573 nm)

(110)

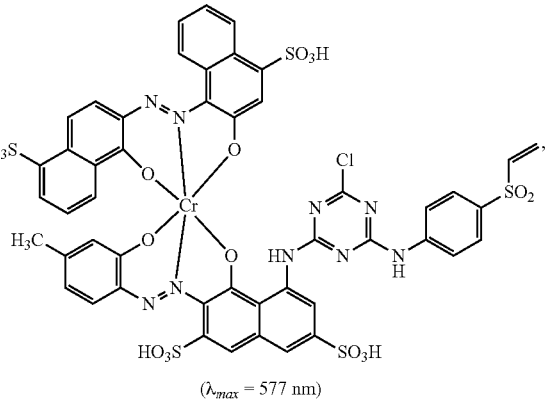

($\lambda_{max}$ = 577 nm)

(111)

($\lambda_{max}$ = 591 nm)

(112)

($\lambda_{max}$ = 579 nm)

can be obtained in an analogous manner to that described in Example 1 (in addition to the dyes of formulae (102) to (112) disclosed in the form of formulae, the disclosure is to be regarded as also including the corresponding coordination isomers).

Dyeing Procedure 1:

10 parts of polyamide 6,6 fibre material (Helanca tricot) are dyed in 500 parts of an aqueous liquor which is adjusted to pH 3 using acetic acid. The proportion of the dye according to Example 1 is 2% based on the fibre weight. The dyeing time at a temperature of 98° C. is from 30 to 90 minutes. The dyed fibre material is then removed, rinsed with water and freed of unfixed dye in a soda wash at pH 10 to 11.5 and 70 to 90° C. in the course of from 20 to 30 minutes. After being rinsed with water again and acidified to pH 4 in an acetic acid bath, the fibre material is dried. Navy dyeings having unsurpassed light- and wet-fastness properties are obtained.

Dyeing Procedure 2:

70 g of a blend fabric consisting of 72% polyamide microfibres and 28% elastane are treated in a dyeing apparatus for 10 minutes at 40° C. with 1.5 liters of liquor containing 3 g of formic acid, 0.4 g of wetting agent and 0.7 g of a levelling agent. The pH of the liquor is 2.9. 3.8 g of the dye according to Example 1, dissolved beforehand in a small amount of water, are then added. The material to be dyed is treated for 5 min. at 40° C. in the dyeing liquor and is then heated to 100° C. and dyed for 20 min. at that temperature. 14 g of calcium chloride are subsequently added and then dyeing is carried out for 40 min. After dyeing, the material is treated for 20 min. at from 70 to 90° C. using 1.5 liters of an after-treatment bath containing 2 g of 1,6-hexamethylenediamine. The material is then rinsed and finished in conventional manner. A deep level dyeing having very good fastness properties is obtained (fastness to washing according to AATCC 16E: note 5).

In order to improve the fastness properties further, a conventional after-fixing step or an alkaline after-treatment can be added. For the alkaline after-treatment, the dyeing is treated for 20 minutes at from 60 to 80° C. in a fresh bath containing 2 g/l of soda and having a pH of 9.2.

Dyeing Procedure 3:

A dye bath which, per 1000 parts of dye bath, contains 3 parts of the dye according to Example 1 and also 1 part of a commercially available thickener, 1 part of a non-ionic wetting agent and the amount of citric acid necessary to give the dye bath a pH of 5.0, is used for the continuous dyeing of a polyamide 6,6 woven carpet material. The woven carpet material is then fixed in steam for 5 min. at 100° C., and washed and dried in customary manner. The woven carpet material is distinguished by a uniform navy blue dyeing having good fastness properties.

Dyeing Procedure 4:

10 parts of woolen knitting yarn are stirred at 30° C. into a dye bath that contains 1.6 parts of the dye according to Example 1, 0.5 part sodium sulfate and 2 parts sodium acetate per 100 parts water and that has been adjusted to a pH value of 4.5 using acetic acid (80%). The liquor is brought to the boil in the course of 45 minutes and maintained at boiling temperature for a further 45 to 70 minutes. The dyed material is then removed, rinsed thoroughly with cold water and dried. A navy blue dyeing having very good fastness properties is obtained.

Printing Procedure I (a) Mercerised cotton satin is pad-dyed with a liquor containing 30 g/l of sodium carbonate and 50 g/l of urea (70% liquor pick-up) and dried.

(b) Using a drop-on-demand ink-jet head (bubble jet), the cotton satin pretreated according to Step (a) is printed with an aqueous ink containing 15% by weight of the reactive dye of formula (101) according to Example 1, 15% by weight of 1,2-propylene glycol and 70% by weight of water.

The print is dried completely and fixed in saturated steam for 8 minutes at 102° C., cold-rinsed, washed off at the boil, rinsed again and dried.

What is claimed is:

1. A reactive dye of formula

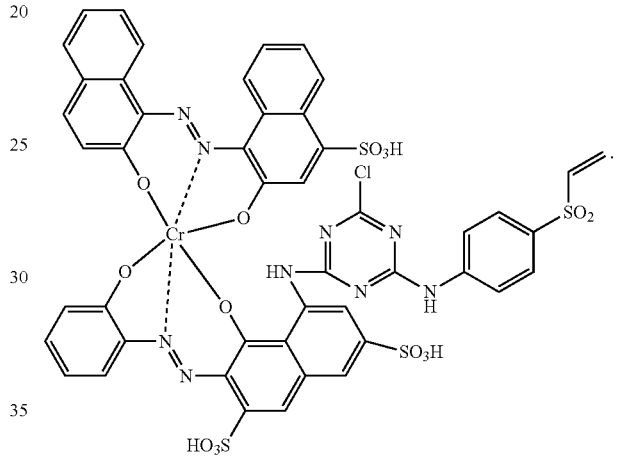

(101)

2. An aqueous ink that comprises a reactive dye of formula (101) according to claim 1.

3. A process for printing textile fibre material, paper or plastics film according to the ink-jet printing method, which comprises spraying individual droplets of the aqueous ink of claim 2 from a nozzle onto the textile fibre material, paper or plastic film.

4. A process for dyeing or printing a hydroxyl-group containing or nitrogen-containing fibre material comprising applying the reactive dye of formula (101) according to claim 1 to the fibre material.

5. The process of claim 4 wherein the fibre material is natural or synthetic polyamide fibre material.

* * * * *